US012582379B2

(12) United States Patent
Johnson et al.

(10) Patent No.: US 12,582,379 B2
(45) Date of Patent: Mar. 24, 2026

(54) ULTRASOUND-EQUIPPED CATHETER STYLET SYSTEM

(71) Applicant: SOUNDPASS MEDICAL LLC, Salt Lake City, UT (US)

(72) Inventors: Jordan K. Johnson, Salt Lake City, UT (US); Travis M. Hotchkiss, Salt Lake City, UT (US); Kyril L. Cole, Salt Lake City, UT (US); Matthew C. Findlay, Salt Lake City, UT (US)

(73) Assignee: SOUNDPASS MEDICAL LLC, Salt Lake City, UT (US)

( * ) Notice: Subject to any disclaimer, the term of this patent is extended or adjusted under 35 U.S.C. 154(b) by 27 days.

(21) Appl. No.: 18/622,661

(22) Filed: Mar. 29, 2024

(65) Prior Publication Data

US 2024/0324988 A1 Oct. 3, 2024

Related U.S. Application Data

(60) Provisional application No. 63/493,760, filed on Apr. 2, 2023.

(51) Int. Cl.
 *A61B 8/12* (2006.01)
 *A61B 8/00* (2006.01)
 (Continued)

(52) U.S. Cl.
 CPC .............. *A61B 8/12* (2013.01); *A61B 8/4209* (2013.01); *A61B 8/4254* (2013.01);
 (Continued)

(58) Field of Classification Search
 CPC ....... A61B 8/12; A61B 8/4209; A61B 8/4254;

A61B 8/4411; A61B 8/4483; A61B 8/466; A61B 8/54; A61B 34/10; A61B 34/25; A61B 2034/107; A61B 2034/254; A61B 2034/2063; A61B 34/20; A61B 2034/2051; G16H 40/63
 See application file for complete search history.

(56) References Cited

U.S. PATENT DOCUMENTS

| | | | |
|---|---|---|---|
| 5,471,988 A | * | 12/1995 | Fujio ...................... A61B 8/445 601/3 |
| RE38,030 E | | 3/2003 | Chapelon et al. |

(Continued)

FOREIGN PATENT DOCUMENTS

| | | |
|---|---|---|
| WO | 2025/119780 | 6/2025 |
| WO | 2025/122631 | 6/2025 |

OTHER PUBLICATIONS

PCT Application No. PCT/US24/22400, International Search Report, Aug. 22, 2024.

(Continued)

*Primary Examiner* — Alexei Bykhovski
(74) *Attorney, Agent, or Firm* — KNH LLP

(57) ABSTRACT

Apparatuses, methods, systems, and program products are disclosed for an ultrasound-equipped catheter stylet system. An apparatus includes a catheter and a stylet configured for insertion into the catheter. The stylet includes a shaft having a first end and a second end and an ultrasound transceiver coupled to the first end of the shaft, the ultrasound transceiver configured to transmit and receive an ultrasound signal.

20 Claims, 10 Drawing Sheets

(51) Int. Cl.

| | |
|---|---|
| *A61B 34/00* | (2016.01) |
| *A61B 34/10* | (2016.01) |
| *G16H 40/63* | (2018.01) |

(52) U.S. Cl.

CPC .......... *A61B 8/4411* (2013.01); *A61B 8/4483* (2013.01); *A61B 8/466* (2013.01); *A61B 8/54* (2013.01); *A61B 34/10* (2016.02); *A61B 34/25* (2016.02); *G16H 40/63* (2018.01); *A61B 2034/107* (2016.02); *A61B 2034/254* (2016.02)

(56) References Cited

U.S. PATENT DOCUMENTS

| | | | |
|---|---|---|---|
| 6,725,082 | B2 | 4/2004 | Sati et al. |
| 7,865,236 | B2 | 1/2011 | Cory et al. |
| 8,320,711 | B2 | 11/2012 | Altmann et al. |
| 8,382,674 | B2 | 2/2013 | Webler |
| 8,480,593 | B2* | 7/2013 | Magnin .................... A61B 8/12 600/439 |
| 9,345,450 | B2 | 5/2016 | Corl |
| 9,579,120 | B2 | 2/2017 | Mauldin, Jr. et al. |
| 9,814,390 | B2 | 11/2017 | Piron et al. |
| 10,039,527 | B2 | 8/2018 | Pelissier et al. |
| 10,111,646 | B2 | 10/2018 | Nyez et al. |
| 10,117,564 | B2 | 11/2018 | Frankel et al. |
| 10,123,766 | B2 | 11/2018 | Mouard et al. |
| 10,549,128 | B2 | 2/2020 | Phillips et al. |
| 10,595,816 | B2 | 3/2020 | Tahmasebi Maraghoosh et al. |
| 11,076,825 | B2 | 8/2021 | Nyez et al. |
| 11,185,305 | B2 | 11/2021 | Kruecker et al. |
| 11,253,153 | B2 | 2/2022 | Piron et al. |
| 11,331,150 | B2 | 5/2022 | Jascob et al. |
| 11,504,095 | B2 | 11/2022 | Mauldin et al. |
| 11,877,889 | B2 | 1/2024 | Courtney et al. |
| 11,883,121 | B2 | 1/2024 | Wallace et al. |
| 11,974,832 | B2 | 5/2024 | Migeotte et al. |
| 11,980,497 | B2 | 5/2024 | Sandrin |
| 12,011,191 | B2 | 6/2024 | Hazard, III et al. |
| 12,013,373 | B2 | 6/2024 | Badeau et al. |
| 12,193,872 | B2 | 1/2025 | Brattain et al. |
| 2012/0143029 | A1* | 6/2012 | Silverstein ........... A61B 8/0891 600/374 |
| 2012/0296213 | A1 | 11/2012 | Mauldin et al. |
| 2012/0302875 | A1 | 11/2012 | Kohring |
| 2018/0042517 | A1* | 2/2018 | van der Weide ...... A61B 34/20 |
| 2019/0247130 | A1 | 8/2019 | State et al. |
| 2019/0282201 | A1 | 9/2019 | Mourad et al. |
| 2019/0307331 | A1* | 10/2019 | Saadat ..................... A61B 1/04 |
| 2020/0077981 | A1 | 3/2020 | Grunwald et al. |
| 2020/0178929 | A1 | 6/2020 | Agarwal et al. |
| 2020/0375571 | A1 | 12/2020 | Lorraine et al. |
| 2021/0186622 | A1 | 6/2021 | Hirson et al. |
| 2021/0196230 | A1 | 7/2021 | Govari |
| 2022/0172354 | A1 | 6/2022 | Misener et al. |
| 2022/0225959 | A1 | 7/2022 | Bharat et al. |
| 2023/0285726 | A1* | 9/2023 | Lenfant .............. A61M 27/006 |
| 2023/0330507 | A1 | 10/2023 | Huang et al. |
| 2023/0380800 | A1 | 11/2023 | Dykes et al. |
| 2024/0053470 | A1 | 2/2024 | Xie et al. |
| 2024/0225611 | A1 | 7/2024 | Firouzi et al. |
| 2025/0176942 | A1 | 6/2025 | McLaughlin et al. |

OTHER PUBLICATIONS

Ultra ICE Ultrasound Imaging Catheter, Boston Scientific, 2014, https://www.bostonscientific.com/content/dam/bostonscientific/ep/portfolio-group/Intracardiac%20Ultrasound/ICE/Ultra%20ICE%20Brochure%20EP-201314-AB.pdf.

* cited by examiner

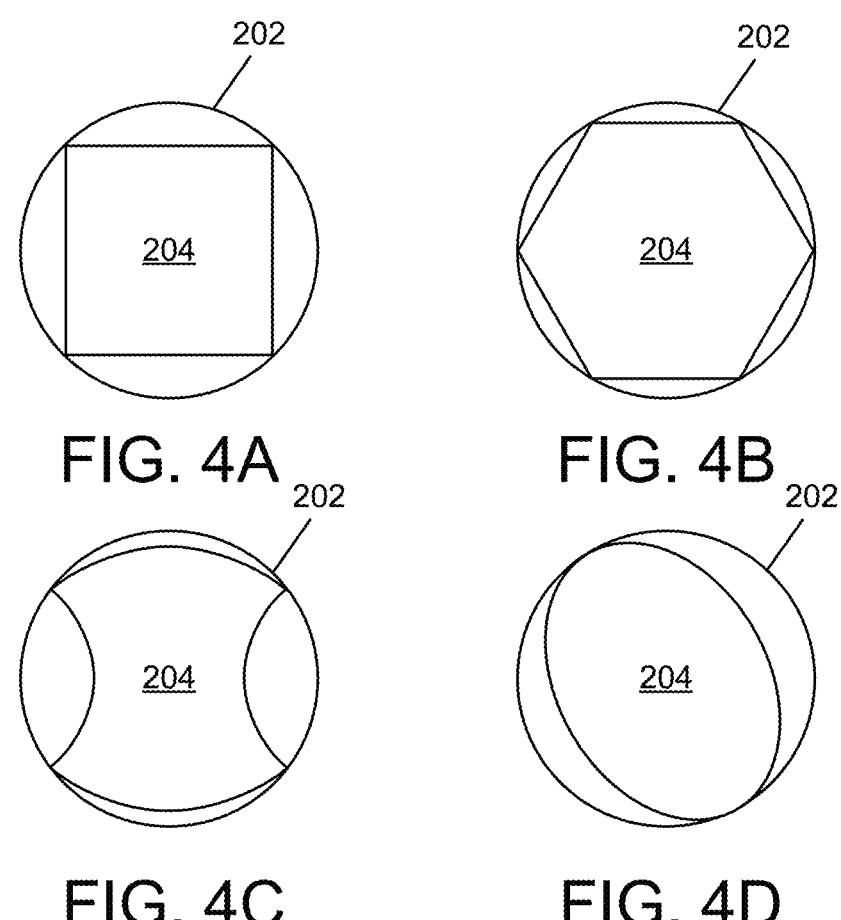
FIG. 4A
FIG. 4B
FIG. 4C
FIG. 4D
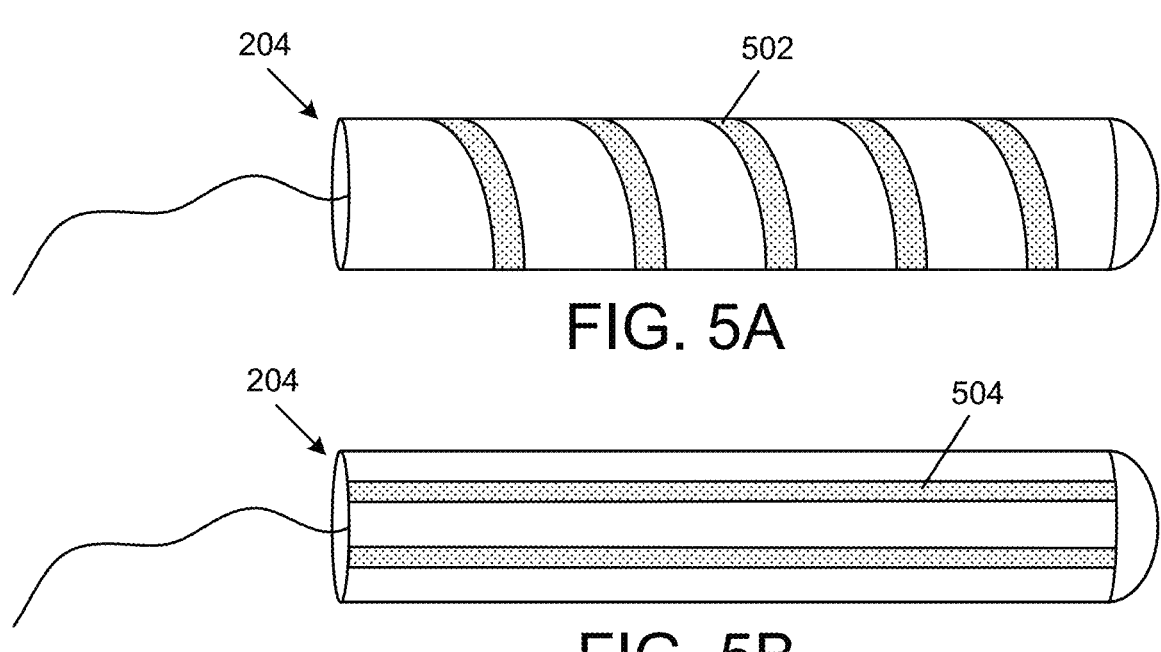
FIG. 5A
FIG. 5B

700

800 receive a signal from the ultrasound transceiver — 802 generate a multi-dimensional graphic based on the received signal — 804 present the multi-dimensional graphic on a display device — 806

900

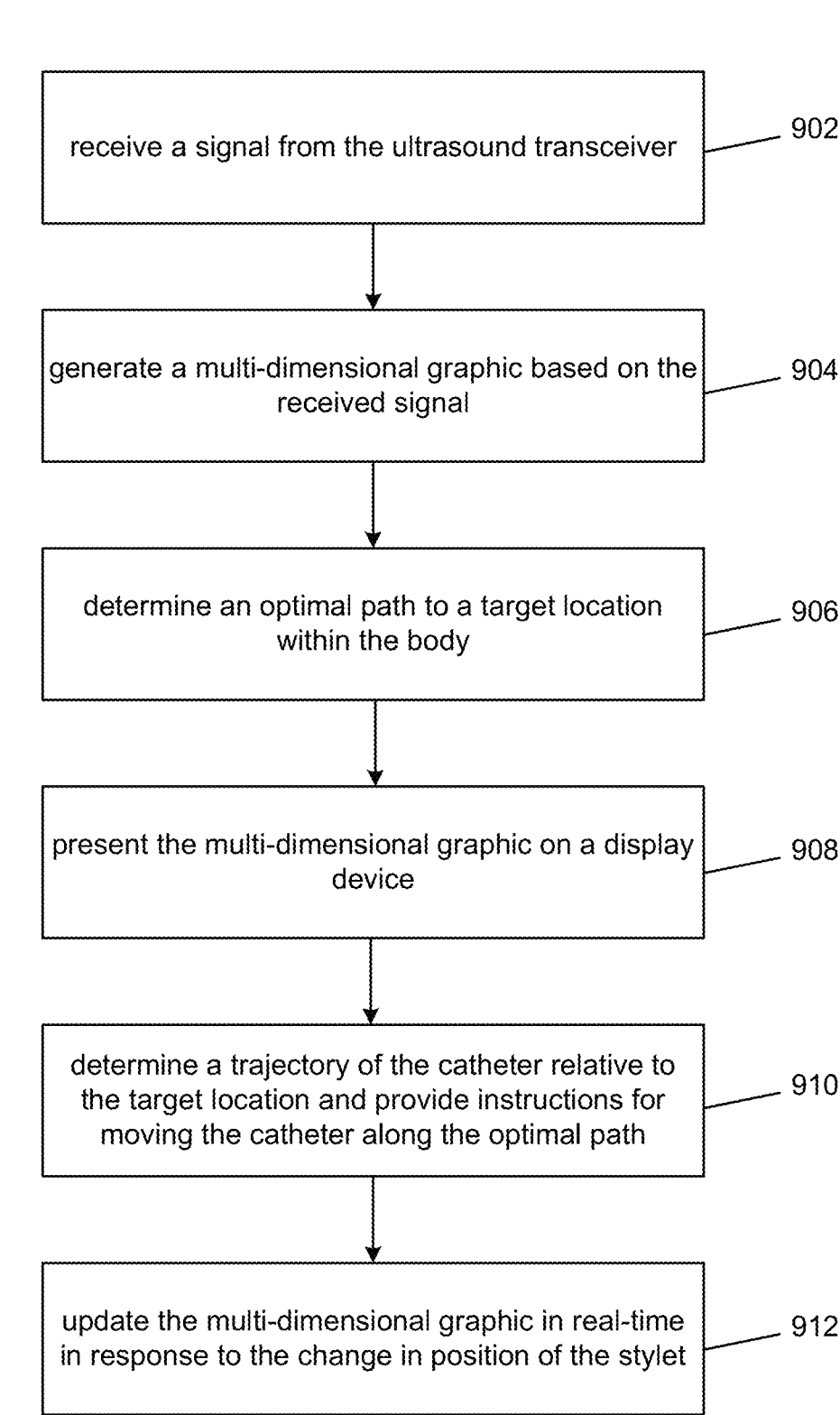

receive a signal from the ultrasound transceiver — 902 generate a multi-dimensional graphic based on the received signal — 904 determine an optimal path to a target location within the body — 906 present the multi-dimensional graphic on a display device — 908 determine a trajectory of the catheter relative to the target location and provide instructions for moving the catheter along the optimal path — 910 update the multi-dimensional graphic in real-time in response to the change in position of the stylet — 912

FIG. 9

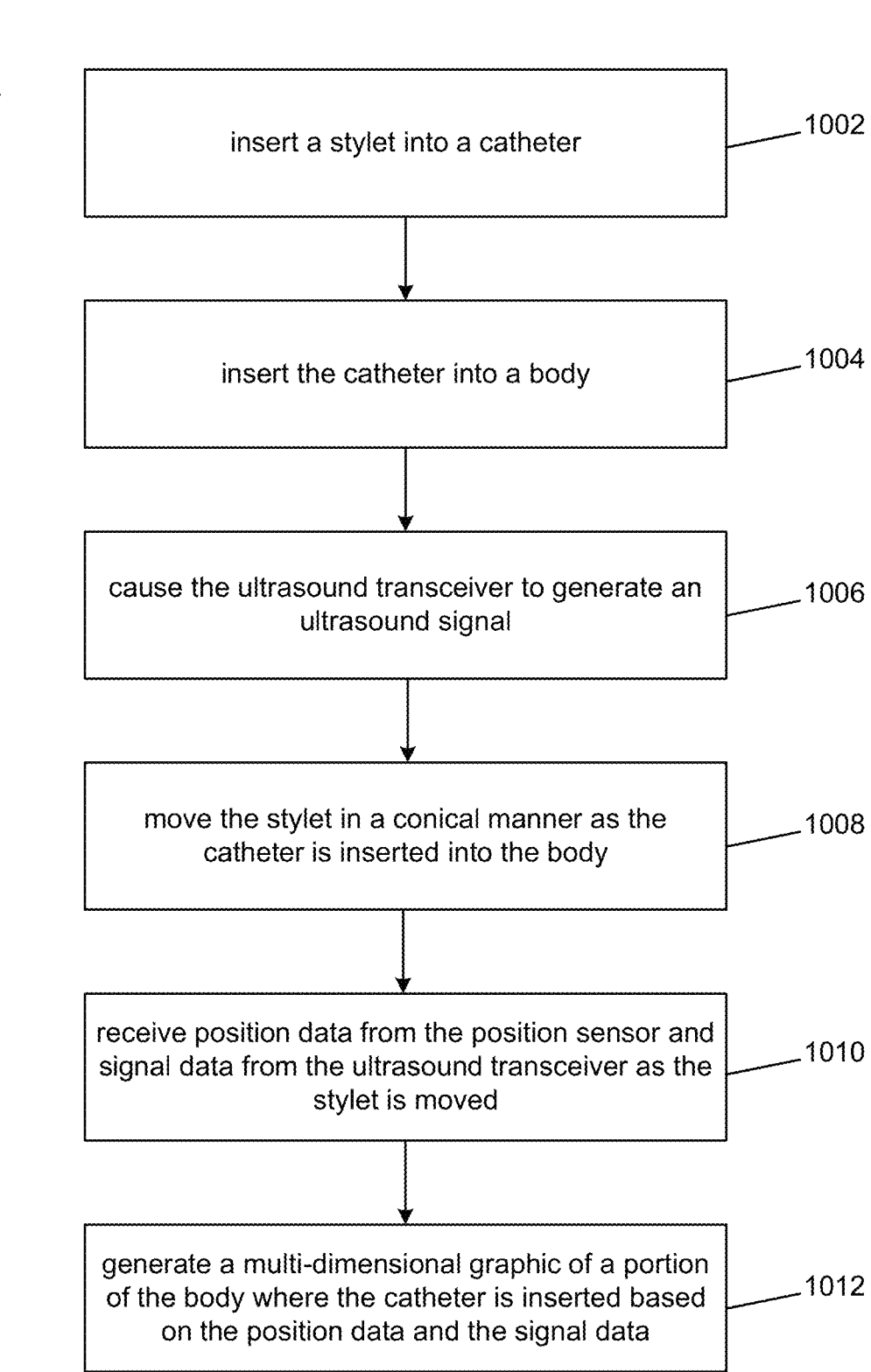

1000 insert a stylet into a catheter — 1002 insert the catheter into a body — 1004 cause the ultrasound transceiver to generate an ultrasound signal — 1006 move the stylet in a conical manner as the catheter is inserted into the body — 1008 receive position data from the position sensor and signal data from the ultrasound transceiver as the stylet is moved — 1010 generate a multi-dimensional graphic of a portion of the body where the catheter is inserted based on the position data and the signal data — 1012

FIG. 10

ULTRASOUND-EQUIPPED CATHETER STYLET SYSTEM

CROSS-REFERENCES TO RELATED APPLICATIONS

This application claims the benefit of U.S. Provisional Patent Application No. 63/493,760 entitled "B-MODE ULTRASOUND-EQUIPPED CATHETER STYLET SYSTEM" and filed on Apr. 2, 2023, for Jordan Keven Johnson et al., which is incorporated herein by reference.

FIELD

This invention relates to imaging and more particularly relates to an ultrasound-equipped catheter stylet system.

BACKGROUND

Diagnostic ultrasound is used in many fields of medicine as a means for identifying anatomical structures and guiding the delivery of needles, instruments, and medicine. Many ultrasound probes have been developed to optimize resolution, depth, and field of view for each specific use, including curvilinear, linear, vaginal, rectal, and cardiac probes.

SUMMARY

An apparatus for ultrasound-equipped catheter stylet system is disclosed. A system and method also perform the functions of the apparatus. In one embodiment, an apparatus includes a catheter and a stylet configured for insertion into the catheter. The stylet, in one embodiment, includes a shaft having a first end and a second end and an ultrasound transceiver coupled to the first end of the shaft, the ultrasound transceiver configured to transmit and receive an ultrasound signal.

In one embodiment, a system includes a catheter and a stylet for insertion into the catheter. In one embodiment, the stylet includes a shaft having a first end and a second end, an ultrasound transceiver coupled to the first end of the shaft, the ultrasound transceiver configured to transmit and receive an ultrasound signal, and a position sensor that detects a position of the stylet relative to a fixed point. In one embodiment, the system is configured to receive a signal from the ultrasound transceiver, generate a multi-dimensional graphic based on the received signal, and present the multi-dimensional graphic on a display device.

In one embodiment, a method is configured to insert a stylet into a catheter, insert the catheter into a body, cause the ultrasound transceiver to generate an ultrasound signal, move the stylet in a conical manner as the catheter is inserted into the body, receive position data from the position sensor and signal data from the ultrasound transceiver as the stylet is moved, and generate a multi-dimensional graphic of a portion of the body where the catheter is inserted based on the position data and the signal data.

BRIEF DESCRIPTION OF THE DRAWINGS

In order that the advantages of the invention will be readily understood, a more particular description of the invention briefly described above will be rendered by reference to specific embodiments that are illustrated in the appended drawings. Understanding that these drawings depict only typical embodiments of the invention and are not therefore to be considered to be limiting of its scope, the invention will be described and explained with additional specificity and detail through the use of the accompanying drawings, in which:

FIG. 4A depicts one embodiment of a stylet within a catheter, in accordance with the subject matter disclosed herein;

FIG. 4B depicts one embodiment of a stylet within a catheter, in accordance with the subject matter disclosed herein;

FIG. 4C depicts one embodiment of a stylet within a catheter, in accordance with the subject matter disclosed herein;

FIG. 4D depicts one embodiment of a stylet within a catheter, in accordance with the subject matter disclosed herein;

FIG. 5A depicts on embodiment of a stylet shaft configuration, in accordance with the subject matter disclosed herein;

FIG. 5B depicts on embodiment of a stylet shaft configuration, in accordance with the subject matter disclosed herein;

FIG. 9 depicts one embodiment of a method for an ultrasound-equipped catheter stylet system, in accordance with the subject matter disclosed herein; and FIG. 10 depicts one embodiment of a method for an ultrasound-equipped catheter stylet system, in accordance with the subject matter disclosed herein.

DETAILED DESCRIPTION

Figure 1:
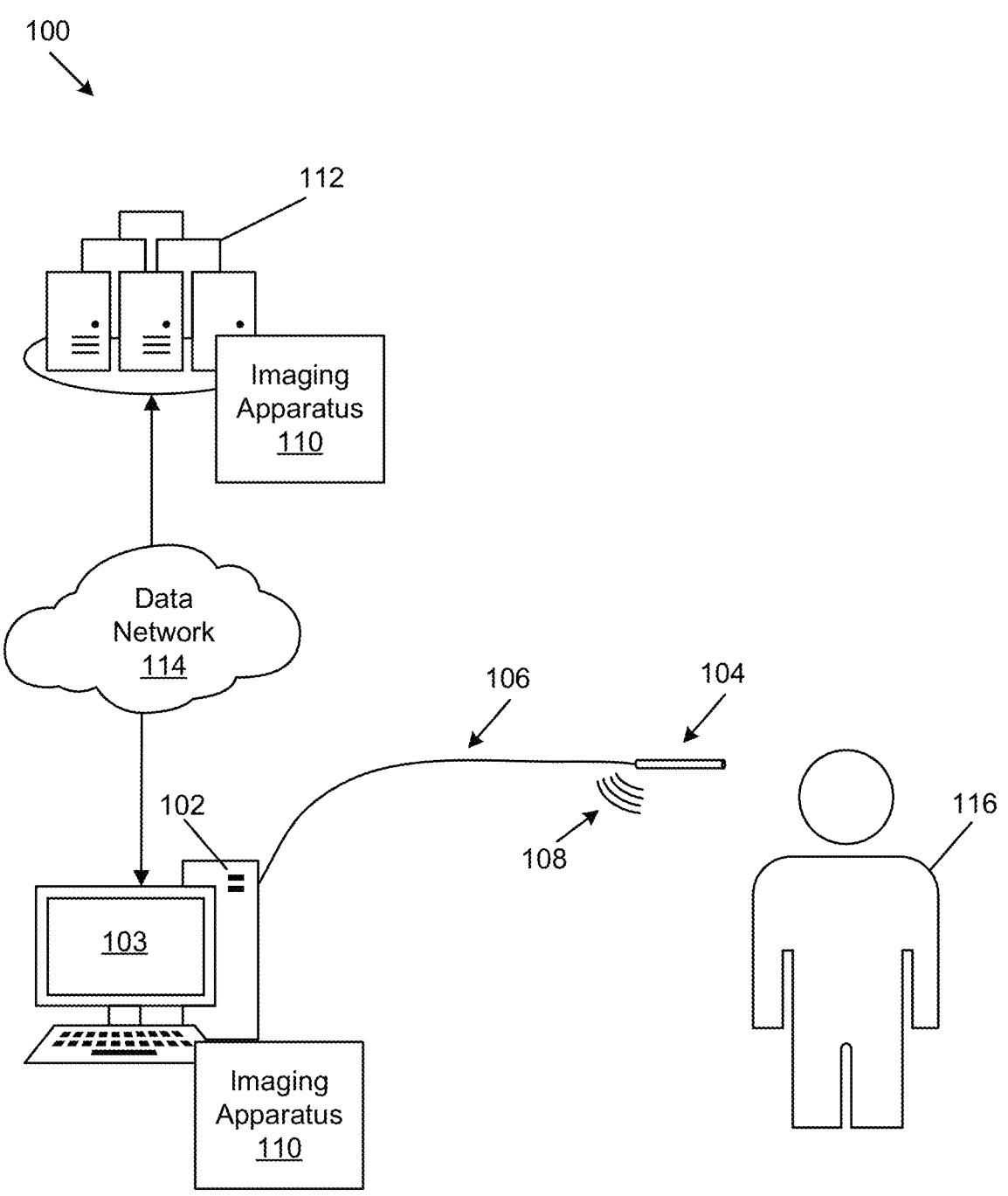
FIG. 1 depicts one embodiment of an ultrasound-equipped catheter stylet system, in accordance with the subject matter disclosed herein.

Diagnostic ultrasound is used in many fields of medicine as a means for identifying anatomical structures and guiding the delivery of needles, instruments, and medicine. Many ultrasound probes have been developed to optimize resolution, depth, and field of view for each specific use, including curvilinear, linear, vaginal, rectal, and cardiac probes. Each of these devices rely on the stabilization of the ultrasound probe superficial to the anatomical structure of interest. These probes then remain superficial to the imaging target while needles, instruments, etc., are advanced towards their target. This approach limits the invasiveness of the procedure or imaging. Unfortunately, the use of ultrasound is limited to applications where a superficial probe can provide adequate imaging to guide deep interventions. This approach also requires significant training to understand and adapt to the limitations of having your imaging and intervention on separate planes.

The utility of ultrasound imaging increases as the output image is representative of known anatomy to the clinician. 3D ultrasound techniques are becoming more and more popular because they translate 2D slices through anatomy to volumetric anatomy. These techniques are already being utilized in multiple fields of medicine, including cardiac electrophysiology, general surgery, and obstetrics. These methods utilize various algorithms to stack B-mode ultrasound slices into volumetric images. These methods are limited by the size of the ultrasound array used to acquire the B-mode images.

As medical technologies become more advanced, there is a need for a method that allows for the utilization of diagnostic ultrasound on a small enough scale to be a piece of the intervention device. As ultrasound transducers decrease in size, there is a significant fall-off of resolution and the ability to use phased arrays or B-mode arrays for imaging. However, B-mode and phased arrays may not be able to approach the physical size required to be a part of an invasive device.

A-mode ultrasound has long been overlooked because it only yields a 1D signal. There are currently only a few applications in medicine where a 1D signal is deemed useful to inform clinical decisions. A-mode transducer technology, on the other hand, does allow for the construction of small enough transducers to be incorporated into an invasive device (<2.0 mm). If a method existed that translated 1D signals into a useful clinical image, diagnostic imaging could be added to most invasive and minimally invasive procedures in medicine.

An external ventricular drain (EVD) is a device used to relieve elevated intracranial pressure in times of obstructed cerebrospinal fluid (CSF) or trapped blood within the brain. As a flexible plastic catheter, the EVD is placed by neurosurgeons or neurointensivists through the brain into one or more ventricles to relieve pressure in the brain, thereby preventing brain herniation, significant morbidity, or death in severe cases. Most often in times of head trauma, where no time exists for adequate imaging prior to EVD placement, a freehand pass technique is done using a patient's anatomical surface landmarks on the skull. As brain bleeds and head trauma may disrupt normal brain anatomy, this freehand pass technique can often lead to surgeons requiring multiple attempts to properly reach the desired ventricle, leading to complications such as additional hemorrhage and inadvertent placement into normal brain tissue.

Conventional EVDs have several limitations and shortcomings that severely limit the surgeon's accuracy, including a lack of real-time understanding of a patient's neuroanatomical changes from normal, a lack of real-time feedback of the surgeon's trajectory accuracy, a lack of real-time objective information to determine a distance to the target, a lack of mid-trajectory adjustability during placement, and a lack of real-time evidence of a ventricle's size.

Based on the foregoing, it is clear that a real-time imaging modality that allows surgeons to view their target in real-time, especially in emergency circumstances, would be of significant utility. The solutions disclosed herein describe an ultrasound-equipped catheter stylet system that meets these objectives. This technology can be utilized in procedures and markets outside of EVD and shunt placement by simply changing the outer diameter of the stylet shaft, ultrasound frequency to adjust for expected target depth, and the catheter that is introduced.

Replacing the standard fish-mouth stylet, often used to pass an EVD catheter into a lateral ventricle, with a stiff stylet device that has an ultrasound transceiver on the tip makes it possible to perform a manual scan and image the underlying brain anatomy. Surgeons or other providers will be able to visualize the ventricular wall interfaces, anechoic fluid-filled ventricles, major vessels, and superficial brain tissue. Real-time imaging enables providers to determine a trajectory and maintain a trajectory for their EVD catheter to pass through the brain into their target, the ventricle. Live imaging during this procedure will further support efficient and accurate EVD placement on the first attempt, limiting adverse effects of pushing a catheter through brain tissue. Accordingly, the subject matter herein is directed to using A-mode ultrasound signals to generate a multi-dimensional image that accounts for the location and orientation of the ultrasound transducer in an inexpensive manner while coupling instrument stereotaxis with real-time imaging.

FIG. 1 depicts one embodiment of an ultrasound-equipped catheter stylet system 100, in accordance with the subject matter disclosed herein. The system 100, in one embodiment, includes a computing device 102, a display device 103, a catheter stylet system 104, an imaging apparatus 110, one or more servers 112, and a data network 114. In certain embodiments, even though a specific number of a computing devices 102, a display devices 103, a catheter stylet systems 104, an imaging apparatuses 110, one or more servers 112, and a data networks 114 are depicted in FIG. 1, one of skill in the art will recognize, in light of this disclosure, that any number of these components may be included in the system 100.

In one embodiment, the system 100 includes one or more computing devices 102. The computing devices 102 may be embodied as one or more of a desktop computer, a laptop computer, a tablet computer, a smart phone, a smart speaker (e.g., Amazon Echo®, Google Home®, Apple HomePod®), an Internet of Things device, a set-top box, a gaming console, a smart TV, a smart watch, an optical head-mounted display (e.g., a virtual reality headset, smart glasses, head phones, or the like), a High-Definition Multimedia Interface ("HDMI") or other electronic display dongle, a personal digital assistant, a digital camera, a video camera, or another computing device comprising a processor (e.g., a central processing unit ("CPU"), a processor core, a field programmable gate array ("FPGA") or other programmable logic, an application specific integrated circuit ("ASIC"), a controller, a microcontroller, and/or another semiconductor integrated circuit device), a volatile memory, and/or a non-volatile storage medium, a display 103, a connection to a display, and/or the like.

In one embodiment, the catheter stylet system 104, which is described in more detail below, is communicatively connected to the computing device 102 via a wired connection 106 and/or a wireless connection 108. In such an embodiment, the wired connection 106 may include a data connection such as an Ethernet connection, a serial bus connection (e.g., a universal serial bus (USB)), a coaxial cable, or the like. In one embodiment, the wireless connection 108 may include a short-range wireless connection such as a Bluetooth® connection, a near-field communication (NFC) connection, a radio frequency (RF) connection, a Wi-Fi connection, and/or the like.

In one embodiment, the imaging apparatus 110 is configured to receive data signals, e.g., ultrasound data signals, from the catheter stylet system 104 (e.g., via the wired 106 or wireless 108 connection) during an EVD or other procedure and generate an image or graphic of the portion of a user's 116 body where the catheter stylet system 104 is inserted to guide and assist a doctor with placement of the catheter. The imaging apparatus 110 is described in more detail below.

In certain embodiments, the imaging apparatus 110 may include a hardware device such as a secure hardware dongle or other hardware appliance device (e.g., a set-top box, a network appliance, or the like) that attaches to a device such as a head mounted display, a laptop computer, a server 112, a tablet computer, a smart phone, a network router or switch, or the like, either by a wired connection (e.g., a USB connection) or a wireless connection (e.g., Bluetooth®, Wi-Fi, near-field communication ("NFC"), or the like); that attaches to an electronic display device (e.g., a television or monitor using an HDMI port, a DisplayPort port, a Mini DisplayPort port, VGA port, DVI port, or the like); and/or the like. A hardware appliance of the imaging apparatus 110 may include a power interface, a wired and/or wireless network interface, a graphical interface that attaches to a display, and/or a semiconductor integrated circuit device as described below, configured to perform the functions described herein with regard to the imaging apparatus 110.

The imaging apparatus 110, in such an embodiment, may include a semiconductor integrated circuit device (e.g., one or more chips, die, or other discrete logic hardware), or the like, such as a field-programmable gate array (FPGA) or other programmable logic, firmware for an FPGA or other programmable logic, microcode for execution on a microcontroller, an application-specific integrated circuit (ASIC), a processor, a processor core, or the like. In one embodiment, the imaging apparatus 110 may be mounted on a printed circuit board with one or more electrical lines or connections (e.g., to volatile memory, a non-volatile storage medium, a network interface, a peripheral device, a graphical/display interface, or the like). The hardware appliance may include one or more pins, pads, or other electrical connections configured to send and receive data (e.g., in communication with one or more electrical lines of a printed circuit board or the like), and one or more hardware circuits and/or other electrical circuits configured to perform various functions of the imaging apparatus 110.

The semiconductor integrated circuit device or other hardware appliance of the imaging apparatus 110, in certain embodiments, includes and/or is communicatively coupled to one or more volatile memory media, which may include but is not limited to random access memory (RAM), dynamic RAM (DRAM), cache, or the like. In one embodiment, the semiconductor integrated circuit device or other hardware appliance of the imaging apparatus 110 includes and/or is communicatively coupled to one or more non-volatile memory media, which may include but is not limited to: NAND flash memory, NOR flash memory, nano random access memory (nano RAM or NRAM), nanocrystal wire-based memory, silicon-oxide based sub-10 nanometer process memory, graphene memory, Silicon-Oxide-Nitride-Oxide-Silicon (SONOS), resistive RAM (RRAM), programmable metallization cell (PMC), conductive-bridging RAM (CBRAM), magneto-resistive RAM (MRAM), dynamic RAM (DRAM), phase change RAM (PRAM or PCM), magnetic storage media (e.g., hard disk, tape), optical storage media, or the like.

In one embodiment, the one or more servers 112, in one embodiment, may be embodied as blade servers, mainframe servers, tower servers, rack servers, and/or the like. The one or more servers 112 may be part of a data center, may be a cloud server, may be located remotely and/or locally to the computing device 102, and/or the like. The one or more servers 108 may be communicatively coupled (e.g., networked) over a data network 114 to the computing device 102 and may be configured to execute or run signal processing, image processing, artificial intelligence (AI), and/or machine learning algorithms, programs, applications, processes, and/or the like.

The data network 106, in one embodiment, includes a digital communication network that transmits digital communications. The data network 106 may include a wireless network, such as a wireless cellular network, a local wireless network, such as a Wi-Fi network, a Bluetooth® network, a near-field communication (NFC) network, an ad hoc network, a mesh network, and/or the like. The data network 106 may include a wide area network (WAN), a storage area network (SAN), a local area network (LAN), an optical fiber network, the internet, or other digital communication network. The data network 106 may include two or more networks. The data network 106 may include one or more servers, routers, switches, and/or other networking equipment. The data network 106 may also include one or more computer readable storage media, such as a hard disk drive, an optical drive, non-volatile memory, RAM, or the like.

The wireless connection may be a mobile telephone network. The wireless connection may also employ a Wi-Fi network based on any one of the Institute of Electrical and Electronics Engineers (IEEE) 802.11 standards. Alternatively, the wireless connection may be a Bluetooth® connection. In addition, the wireless connection may employ a Radio Frequency Identification (RFID) communication including RFID standards established by the International Organization for Standardization (ISO), the International Electrotechnical Commission (IEC), the American Society for Testing and Materials® (ASTM®), the DASH7™ Alliance, and EPCGlobal™.

Alternatively, the wireless connection may employ a ZigBee® connection based on the IEEE 802 standard. In one embodiment, the wireless connection employs a Z-Wave® connection as designed by Sigma Designs®. Alternatively, the wireless connection may employ an ANT® and/or ANT+® connection. The wireless connection may be an infrared connection including connections conforming at least to the Infrared Physical Layer Specification (IrPHY) as defined by the Infrared Data Association® (IrDAR). Alternatively, the wireless connection may be a cellular telephone network communication.

Figure 2:
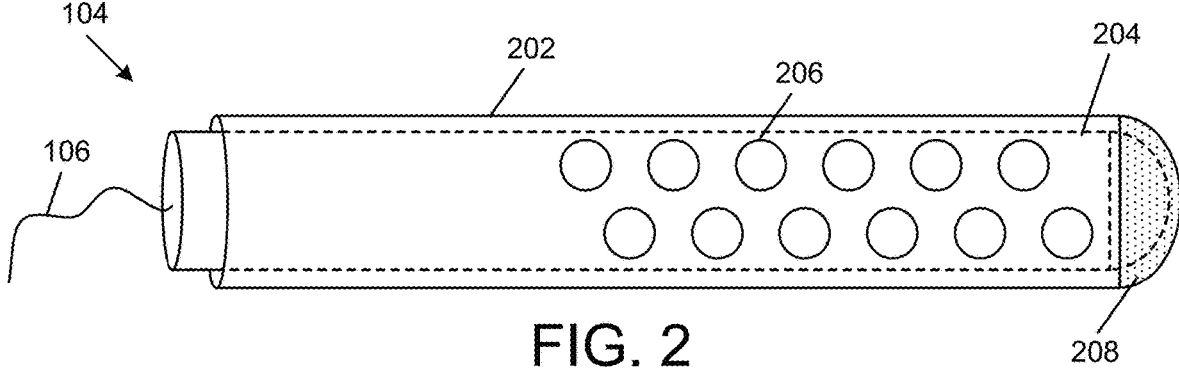
FIG. 2 depicts one embodiment of a catheter stylet system, in accordance with the subject matter disclosed herein.

FIG. 2 depicts one embodiment of a catheter stylet system 104, in accordance with the subject matter disclosed herein. In one embodiment, the catheter stylet system 104 includes a catheter 202 and a stylet 204. As used herein, a catheter 202 may refer to a flexible tube that is inserted through a narrow opening into a body cavity, e.g., into a user's head, a bladder, or the like. In one embodiment, the catheter 202 is comprised of a flexible tubing such as latex, polyurethane, or silicone. The catheter 202 may include a plurality of openings 206, slits, holes, or the like to allow fluid to enter the catheter 202 and be drained from the body. In one embodiment, the catheter 202 includes measurement lines or guides along the outer surface that are used to indicate a depth of insertion of the catheter 202.

As it relates to the subject matter herein, the end of the catheter 202 may include a tip 208 that is used to help guide the catheter 202 through the body, e.g., through tissue and other material. In one embodiment, the tip 208 is made of an echolucent material. As used herein, the echolucent material may comprise material that is translucent to ultrasonic waves, e.g., ultrasound waves. Thus, in such an embodiment, a tip 208 that is echolucent allows ultrasound waves, e.g., transmitted from the stylet 204, to travel through the tip without much, if any, interference. In one embodiment, the echolucent tip has a configuration that filters or focuses the ultrasound signal. Such a configuration may include a shape of the echolucent tip, a size of the echolucent tip, a thickness of the echolucent tip, a presence of cavities within the echolucent tip, or a combination thereof.

Figure 3:
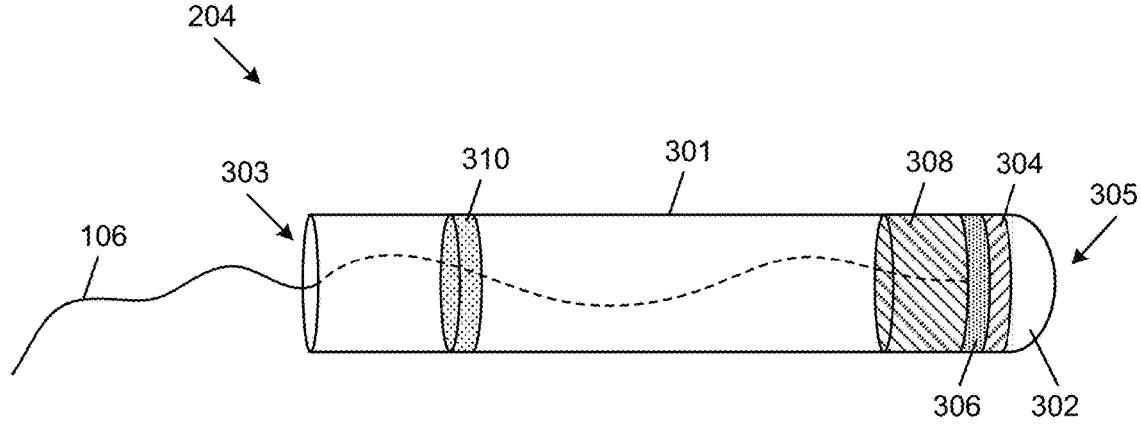
FIG. 3 depicts one embodiment of a stylet, in accordance with the subject matter disclosed herein.

FIG. 3 depicts one embodiment of a stylet 204, in accordance with the subject matter disclosed herein. The stylet 204 may include a shaft 301 with a proximal end 303 and a distal end 305. The stylet 204 may be sized, shaped, or otherwise configured to fit into a catheter, e.g., the catheter 202 described above with reference to FIG. 2. The stylet 204 may be made of a substantially rigid material such as plastic, metal (e.g., stainless steel), polymers, or the like. In one embodiment, the stylet 204 can be a single-use device or can be sterilized for reusability.

In one embodiment, the stylet 204 comprises various components. The stylet 204, in certain embodiments, includes an acoustic lens 302 for focusing ultrasound waves or signals from an ultrasound transceiver 306. The stylet 204, in one embodiment, includes an acoustic matching layer 304, which provides the acoustic impedance gradient for the acoustic energy from the transceiver 306 to penetrate the body tissue and for the reflected acoustic waves (the returning echo) to return to the transceiver 306 for detection.

In one embodiment, the transceiver 306 includes an ultrasound transceiver, but could be any type of transceiver that is capable of transmitting and receiving ultrasonic waves or signals. In one embodiment, the transceiver 306 includes a transducer, e.g., of Piezoelectric material, which is configured to convert received ultrasound signals or echoes to a signal that is transmitted to the computing device 102.

The transceiver 306 may be configured to transmit ultrasound signals according to a predetermined pattern and/or with a predetermined spread. In certain embodiments, the transceiver 306 is communicatively coupled to a computing device 102 over a wired connection 106 or a wireless connection 108 to receive configuration information, e.g., a pattern, a spread, a signal strength, a frequency, or other configuration of the transceiver 306, and to send signal information to the computing device 102 from waves received in response to the transmission of ultrasound waves from the transceiver 306.

In one embodiment, the ultrasound transceiver 306 is configured to transmit and receive A-mode ultrasound signals. A-mode ultrasound signals, as used herein, may refer to ultrasound signals generated by a single transceiver that scans a line through the body with the echoes capable of being plotted as a function of depth. In some embodiments, the ultrasound transceiver 306 is configured to transmit and receive B-mode ultrasound signals, which, as used herein, may refer to ultrasound that uses an array of transceivers to scan a plane through the body. In such an embodiment, the stylet 204 includes a plurality of transceivers 306 that are configured to send and receive a plurality of ultrasound signals.

In one embodiment, the transceiver 306 may be shaped according to the application and target of the ultrasound signals. For instance, the transceiver 306 may have a concave-focusing transmitter face, a flat transmitter face, a convex-focusing transmitter face, or the like. In certain embodiments, concave-focusing transmitter faces allow for the best resolution and may be the most effective for applications with size constraints, e.g., for a EVD application that has a small entry point, e.g., a diameter <2.5 mm.

In one embodiment, the focal radius of the transceiver 306 can be designed to have a beneficial focusing interaction with the catheter tip 208 and/or the acoustic lens 302. The shape of the catheter tip 208 and/or the acoustic lens 302 can be configured to further focus the ultrasound signal, which improves resolution and allows for more accurate imaging. Passing the ultrasound wave through multiple angled, curved, or strategically shaped surfaces or volumes can focus the ultrasound waves using diffraction.

One form of this multi-dimensional volume reconstruction can use representative cylindrical, prismatic, or beam-specific near zone or far zone volumes from the A-mode transducer signal. These representative signal volumes are specific to the transducer utilized. The transducer design elements or finite element modeling of the beam spread pattern can inform the representative signal volume shape. Transducer-specific representative volumes allow for more accurate multi-dimensional reconstruction throughout various depths.

In one embodiment, the ultrasound transceiver 306 is detachable from the shaft 301 prior to removing the stylet 204 from the catheter 202. In such an embodiment, the shaft 301 may include a mechanism for detaching the ultrasound transceiver 306 from the shaft 301 such as a button or the like, which decouples or disconnects the ultrasound transceiver 306 from the shaft 301. In this manner, the ultrasound transceiver 306 may be implantable in a patient for continued monitoring.

In one embodiment, the stylet 204 includes a backing layer 308. The backing layer 308, in one embodiment, prevents sound waves from reflecting back into the transceiver, where they can cause noise. Further, the backing layer 308 may impact the sound wave's characteristics, such as its sensitivity and signal to noise ratio.

In one embodiment, the stylet 204 includes other components such as a position sensor 310. The position sensor 310 may include an induction coil sensor or sensors that are configured to detect change in position such as an inertial measurement unit (IMU) sensor, an accelerometer, a gyroscope, an angel transducer, and/or the like. The positioning information may be transmitted to the computing device 102 and used to further construct an image or graphic that is generated using the ultrasound signals. For example, a fixed point relative to the position sensor 310 may be referenced at the distal end of the stylet where the ultrasound transceiver 306 is located. As the stylet 204 is moved in a conical manner, this creates a conical map of device movement that the position sensor 310 can sense at a known position proximal to the device tip. As explained in more detail below, sensed positioning of the proximal device within this conical map allows for the splicing of 1D data into 2D or 3D images.

FIGS. 4A-4D depict stylets 204 of differing shapes within a catheter 202, in accordance with the subject matter disclosed herein. In certain embodiments, EVD and other applications for draining fluid from parts of the body are dependent on the capacity of the catheter 202 to allow fluid such as CSF to drain from the ventricle and indicate to the surgeon that the ventricular space has been breached. Ideally the lumen of the catheter 202 is not entirely filled such that the rigid material which occupies the lumen can be bypassed and indicate to surgeons that the ventricular space has been breached based on the presence of CSF without requiring that the stylet 204 be removed prior to CSF being externally expressed.

Thus, different configurations for the stylet 204 or stylet tip can be used to allow fluid to bypass or flow around the stylet 204. For example, the stylet 204 may have a square shape (FIG. 4A), a hexagonal shape (FIG. 4B), a machined shape (FIG. 4C), or an elliptical shape (FIG. 4D). As shown in each of FIGS. 4A-4D, the shape of the stylet 204 creates space between the catheter 202 and the stylet 204, which allows fluid to flow around or bypass the stylet 204 and out the end of the catheter 202.

FIGS. 5A and 5B depict stylets 204 with different shaft configurations, in accordance with the subject matter disclosed herein. Another way to create space between the stylet 204 and the catheter 202 and allow fluid to flow around or bypass the stylet 204, is to introduce grooves, riflings, channels, or the like in the stylet shaft 301. FIG. 5A depicts a stylet shaft 301 with riflings engraved, formed, or cut into the shaft 301 and FIG. 5B depicts a stylet shaft 301 with channels or grooves engraved, formed, or cut into the shaft 301. In either embodiment, when the stylet 204 is inserted into the catheter 202 and the catheter 202 is inserted into a portion of a body, as the catheter 202 is inserted, fluid from the body is able to bypass the stylet 204 and drain through the catheter 202. In this manner, fluids such as CSF can be expressed without the stylet 204 being removed from the catheter 202, while optimizing stylet 204 stiffness for handling and maximizing the outer diameter for optimal imaging and resolution.

Figure 6A:
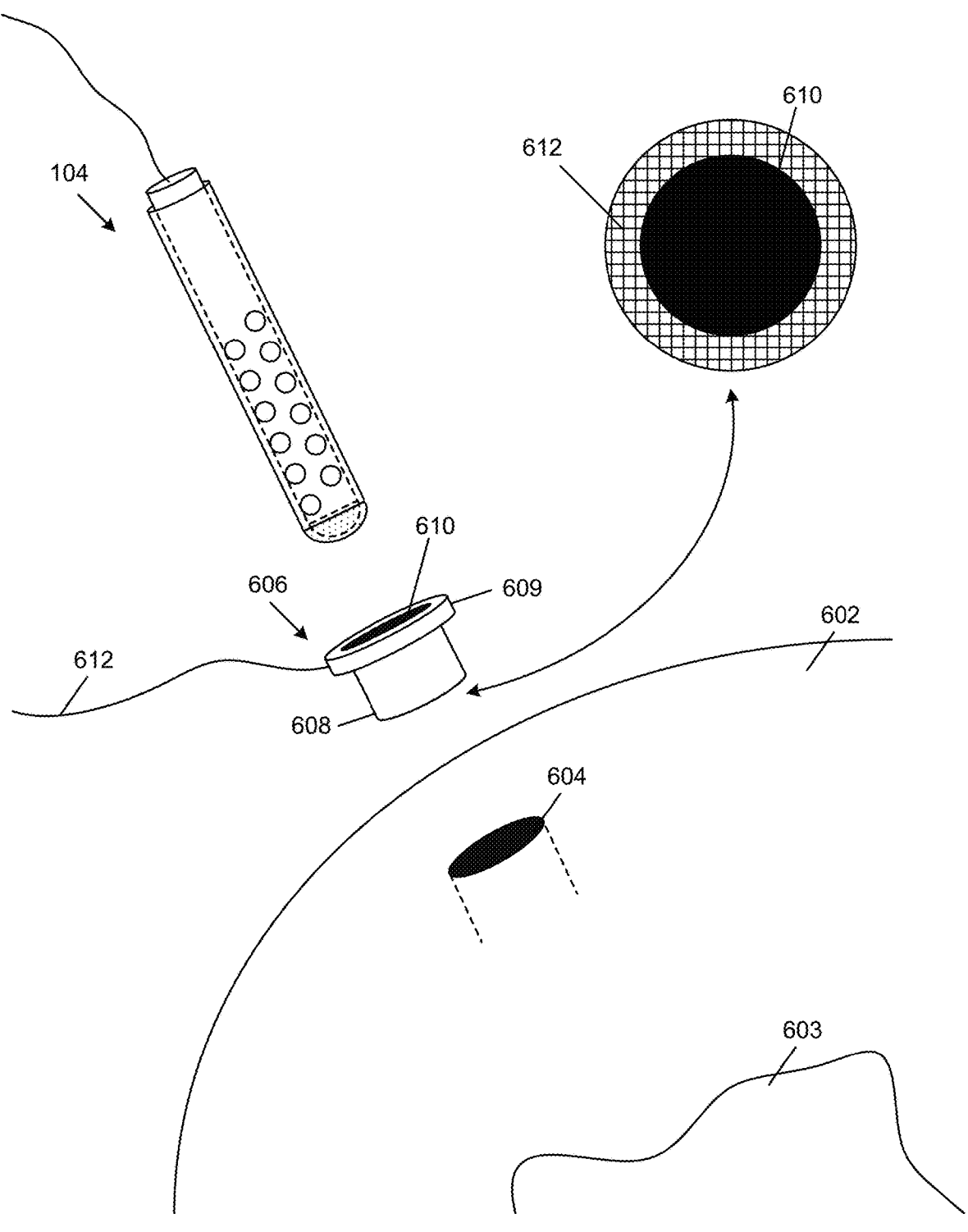
FIG. 6A depicts one embodiment of a catheter stylet system being inserted into a body, in accordance with the subject matter disclosed herein.

FIG. 6A depicts one embodiment of a catheter stylet system 104 being inserted into a body, in accordance with the subject matter disclosed herein. In one embodiment, the catheter stylet system 104 includes an anchor device 606 that is inserted into the opening 604 or bore hole on the body 602, here in the skull of a user's head. In one embodiment, the anchor device 606 includes an insertion portion 608, which goes into the opening 604 and a lip portion 609 that sits on top of the outer edge of the opening 604. An opening 610 through the anchor device 606 allows the catheter stylet system 104 to pass through the anchor device 606 and into the body 602, e.g., the skull and into a fluid-filled portion of the body, such as a ventricle 603.

In one embodiment, the anchor device 606 is configured to stabilize the catheter stylet system 104, e.g., the ultrasound tip to ensure that ultrasound data is captured from the same location. Anchor devices 606 may include pins, screws, or other commonly used neurosurgery hardware, straps that can be placed around the patient's cranium, and/or a deployable balloon for stabilization. For example, a deployable balloon device may be spherical or cylindrical in shape and includes a hollow cylindrical center for the catheter stylet system 104 to advance through. The hollow cylindrical center may be lined with a plastic or metal cylinder, which will in turn be lined by an inflatable membrane. The membrane may inflate in a cylindrical fashion and press against the bone of the cranium to allow fixation of the catheter stylet system 104 in two directions while still allowing advancement of the catheter stylet system 104 and limited flexion of the device to search for the ventricles.

Fixation of the catheter stylet system 104 may help to facilitate the multi-dimensional construction of images, described in more detail below, which will facilitate a real-time understanding of the patient's neuroanatomy, real-time feedback of the surgeon's trajectory, real-time distance from target information, real-time evidence of the ventricle's size, and information or data on how a surgeon should adjust their trajectory mid-pass, if needed.

In one embodiment, the anchor device 606 may include transceivers 612, such as a phased array of A-mode and/or B-mode ultrasound transceivers on a bottom portion of the anchor device 606, that are also communicatively coupled to a computing device, e.g., via a wire connection 612, that are used to further capture ultrasound data that can be used in the generation of multidimensional images of the portion of the body where the catheter stylet system 104 is inserted.

In further embodiments, means may be provided that allow for steering or deflection of the catheter stylet system 104, thereby allowing for a mid-trajectory adjustment of the catheter 202 placement. The means for mid-trajectory adjustment may include, but are not limited to, two wires running down the outer surface of the stylet 204, e.g., in a space between the inner surface of the catheter 202 and the outer surface of the stylet 204 and attached to the tip of the stylet 204. Pulling on one wire, e.g., through an ergonomic handle, may shorten that wire with respect to the other, thereby pulling or turning the catheter stylet system 104. Simple twisting of the stylet 204 while inserted in the body may allow for corrections to be made in any direction perpendicular to the current advancement line or trajectory. In another embodiment, the stylet 204 may have a braided shaft and a deflectable section that allows for multi-direction changes and correction of the stylet tip trajectory mid-pass. By engaging an actuator on the handle or proximal shaft of the stylet 204, the provider can make fine adjustments to their trajectory.

Figure 6B:
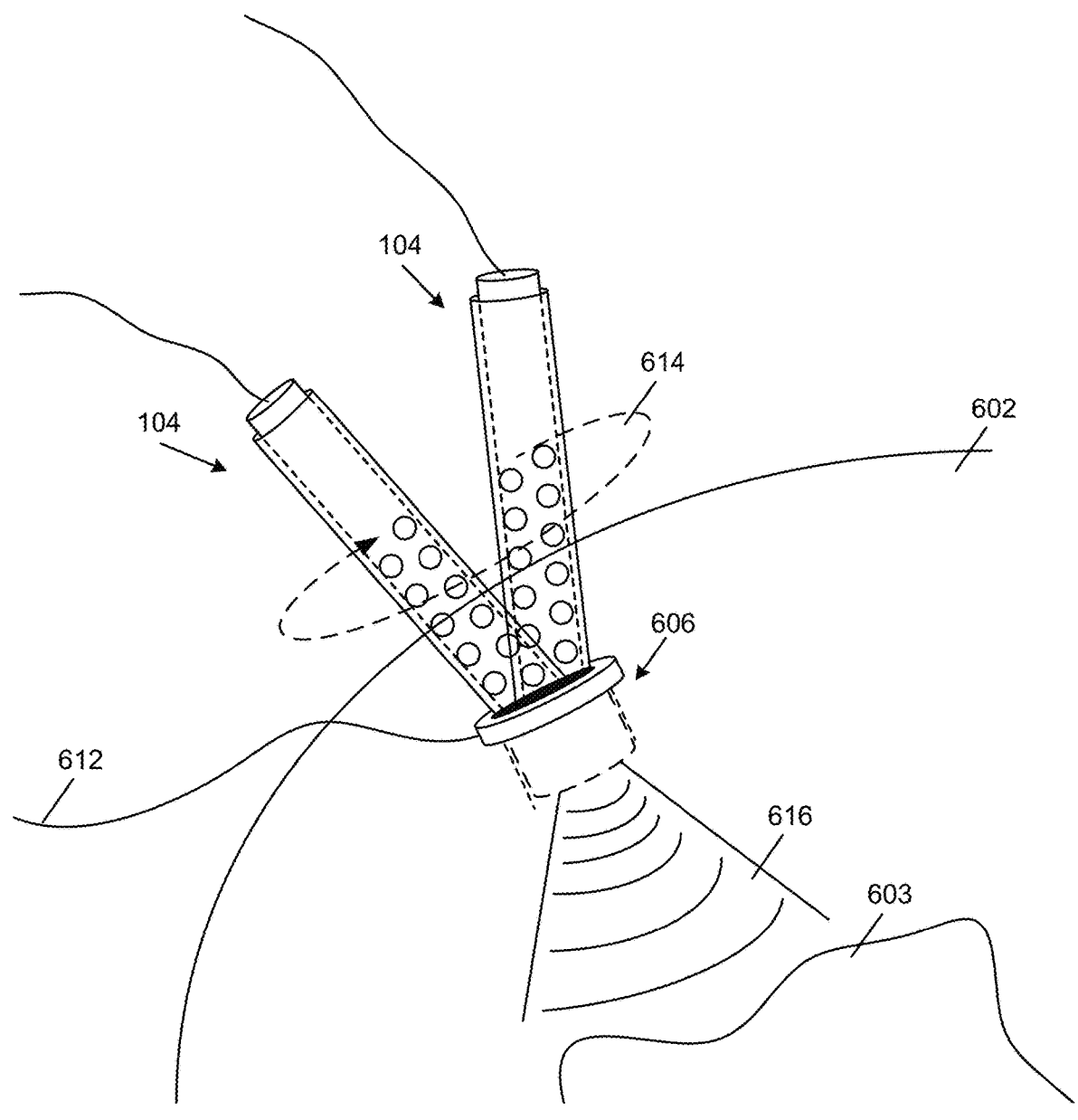
FIG. 6B depicts one embodiment of a catheter stylet system being inserted into a body, in accordance with the subject matter disclosed herein.

FIG. 6B depicts one embodiment of a catheter stylet system 104 inserted into a body, in accordance with the subject matter disclosed herein. In one embodiment, the anchor device 606 is inserted into the opening in the body 602, and the catheter stylet system 104 is inserted into the opening 610 in the anchor device 606 and further into the body 602. The catheter stylet system 104 can then be moved or rotated in a conical fashion direction 614 (e.g., about a rotational axis), which causes the ultrasound signals 616 to be spread in multiple directions within the body 602. Further, the catheter stylet system 104 may capture positional data from a position sensor 310 to detect the conical movements relative to a fixed point, e.g., the tip of the catheter stylet system 104. In this manner, ultrasound data from multiple cross sections of the body 602 can be captured and used to generate multi-dimensional images or graphics, which may be done in real-time in response to detecting the change in position of the catheter stylet system 104.

Figure 6C:
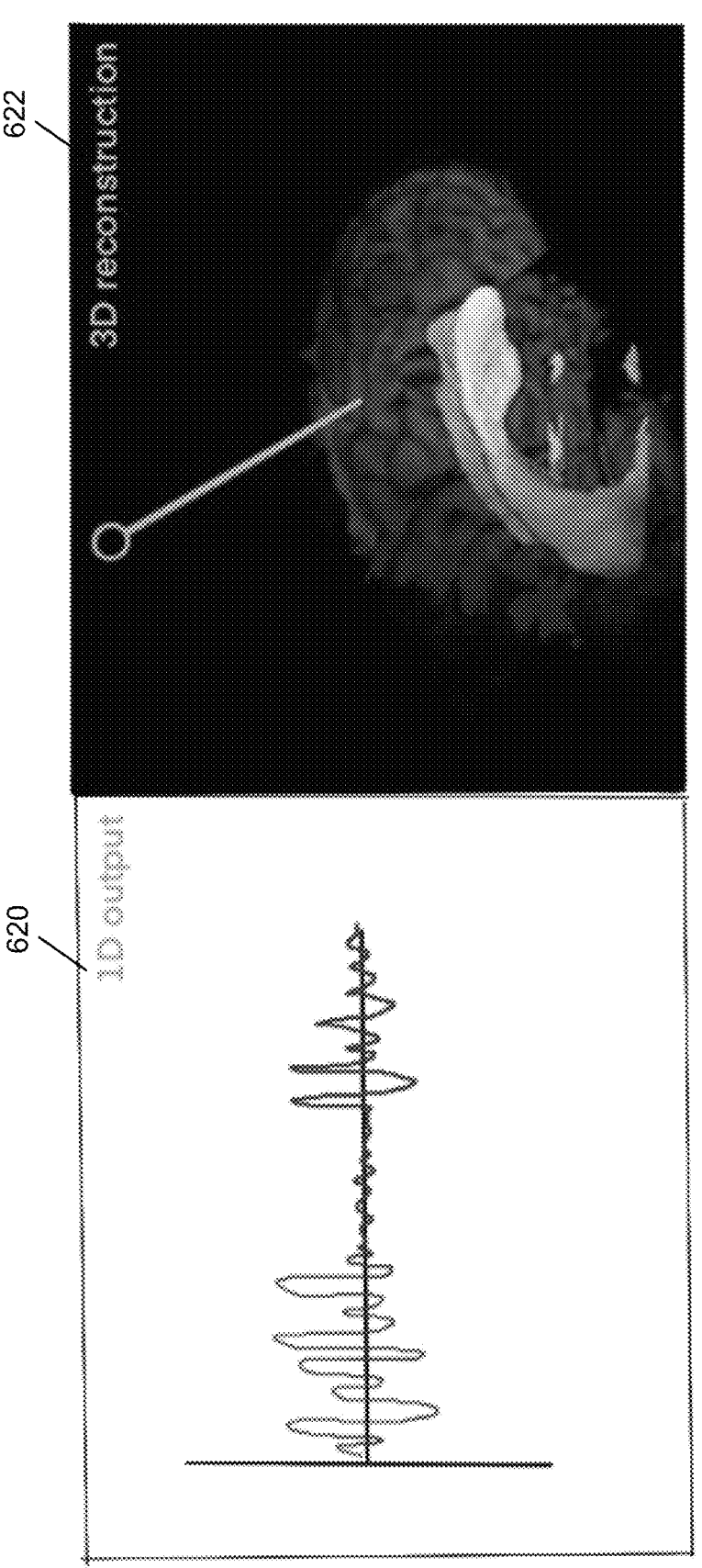
FIG. 6C depicts one embodiment of an output using the catheter stylet system, in accordance with the subject matter disclosed herein.

FIG. 6C depicts one embodiment of an output using the catheter stylet system 104, in accordance with the subject matter disclosed herein. In one embodiment, the catheter stylet system 104 may capture and transmit A-mode ultrasound signals, which generates the 1D output signal 620 shown in FIG. 6C. The 1D output signal 620 may be used to generate a 3D reconstruction of the portion of the body where the catheter stylet system 104 is inserted, e.g., in the brain, by using the 1D output signal 620 to determine a tissue type, material, or the like (e.g., based on the amplitude of the 1D output signal 620), and generating a corresponding 3D graphical image 622, in real-time, as the catheter stylet system 104 is moved into the body in a conical manner, as described in more detail below.

Figure 7:
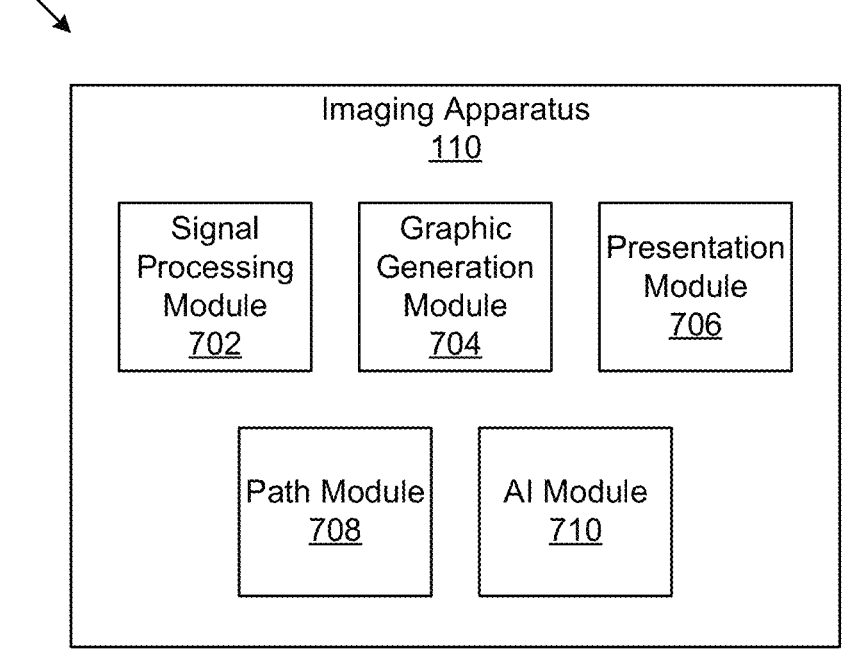
FIG. 7 depicts one embodiment of an apparatus for an ultrasound-equipped catheter stylet system, in accordance with the subject matter disclosed herein.

FIG. 7 depicts one embodiment of an apparatus 700 for an ultrasound-equipped catheter stylet system, in accordance with the subject matter disclosed herein. In one embodiment, the apparatus 700 includes an instance of an imaging apparatus 110. The imaging apparatus 110, in one embodiment, includes a signal processing module 702, a graphic generation module 704, a presentation module 706, a path module 708, and an AI module 710, which are described in more detail below. In one embodiment, the imaging apparatus 110 may be located on the computing device 102, on the servers 112 (e.g., to offload processing to a data center), and/or a combination thereof.

In one embodiment, the signal processing module 702 is configured to receive a signal from the ultrasound transceiver 306 of the catheter stylet system 104. In such an embodiment, as the ultrasound transceiver 306 transmits ultrasound signals or waves and receives an echo an echo signal or wave in return, the ultrasound transceiver 306 transmits information associated with the echo signal or wave to the computing device 102 via a wired 106 or wireless 108 connection.

In one embodiment, the signal processing module 702 may cause the ultrasound transceiver 306 to transmit and receive ultrasound signals at consistent, periodic intervals, e.g., every second, every half second, or the like. In further embodiments, the signal processing module 702 may dynamically determine the rate to transmit and receive ultrasound signals, e.g., during the procedure in response to movement of the catheter stylet system 104 (based on input from a position sensor 310), based on feedback from an AI engine (described below), based on feedback from the received ultrasound signals, in response to user input, and/or the like.

In one embodiment, the signal processing module 702 may determine a pulse pattern for causing the ultrasound transmitter 306 to transmit and receive ultrasound signals. The pulse pattern may include a strength of the signal, a signal frequency, a signal sequence (how often or at what intervals the signal is transmitted), and/or the like. The signal processing module 702 may dynamically determine the rate to transmit and receive ultrasound signals, e.g., during the procedure in response to movement of the catheter stylet system 104 (based on input from a position sensor 310), based on feedback from an AI engine (described below), based on feedback from the received ultrasound signals, in response to user input, and/or the like.

In one embodiment, the signal processing module 702 filters out noisy ultrasound data from the received signal, or data that is not useful for generating the multi-dimensional graphic. Such data may include outlier data, data that cannot be graphically depicted, signal data that is above or below a threshold amplitude, and/or the like. In one embodiment, the signal processing module 702 may use an AI engine to process the signal data, e.g., a 1D output signal, to identify and remove noisy data.

In one embodiment, the graphic generation module 704 is configured to generate a multi-dimensional graphic or image based on the signal that the signal processing module 702 receives. In such an embodiment, the multi-dimensional graphic may be a two-dimensional (2D) or a three-dimensional (3D) graphic of a portion of a body where the catheter stylet system 104 is inserted. For example, as the catheter stylet system 104 is inserted into a patient's head and through the brain to locate a ventricle, the signal processing module 702 may receive and process a 1D output signal from an A-mode ultrasound transceiver 306 in the catheter stylet system 104, which the graphic generation module 704 uses to generate a multi-dimensional graphic of the user's brain as the catheter stylet system 104 is placed within the user's head.

In one embodiment, the graphic generation module 704 uses various image processing algorithms to process the output signal to generate the multi-dimensional graphic. For example, the graphic generation module 704 uses a segmentation algorithm to identify edges, regions, and/or the like of the structure being imaged based on different characteristics of the output signal, e.g., based on different amplitudes, thresholds, values, or the like. For instance, the graphic generation module 704 may use a segmentation algorithm to identify brain tissue, blood vessels, ventricles, and/or other materials, tissues, regions, or the like within the user's brain, and may include metadata or other additional information within the generated graphic that describes the different areas, regions, structures, or the like of the body within the graphic.

In one embodiment, the graphic generation module 704 generates the multi-dimensional graphic based on a change in position of the stylet according to position data received from the position sensor 310. For instance, as the catheter stylet system 104 is moved, e.g., in a conical manner, the signal processing module 702 may receive and process new ultrasound signal data, which the graphic generation module 704 uses to generate the multi-dimensional graphic. In such an embodiment, the graphic generation module 704 may update the multi-dimensional graphic in real-time in response to the change in position of the catheter stylet system 104.

In one embodiment, the presentation module 706 is configured to present the multi-dimensional graphic on a display device 103. In such an embodiment, the presentation module 706 may present the multi-dimensional graphic as it is created and/or received from the graphic generation module 704, e.g., in real-time during the procedure such that the graphic that is presented is continually updated as new graphic data is provided from the graphic generation module 704.

In one embodiment, the presentation module 706 is configured to visually highlight different parts or portions of body that have different properties, e.g., different tissue types, fluid types, materials, and/or the like. For instance, the presentation module 706 may use metadata or other information within the multi-dimensional graphic data that the graphic generation module 704 generates and provides to visually highlight different areas, regions, structures, or the like of the body, e.g., using different brightness levels, contouring, shading, outlines, line thickness, colors, gradients, patterns, labels, text, and/or the like.

In one embodiment, the path module 708 is configured to determine an optimal path to a target location within the body. In such an embodiment, the path module 708 may receive a location of the insertion point on the body for the catheter stylet system 104 relative to predetermined, predefined, or the like known representation of the body where the catheter stylet system 104 is being inserted. For example, on the graphical display, a user such as a doctor may select, point, click, tap, or the like on a representation of a user's head where the catheter stylet system 104 is being inserted.

Based on that reference point, the path module 708 may determine an optimal path to a target point, which may be set by the doctor (e.g., by providing input that identifies the target point), may be determined based on a previous scan of the user's body (e.g., a magnetic resonance imaging (MRI) scan or a computed tomography (CT) scan), based on an AI-generated representation of the body, and/or based on other representative data describing the portion of the body where the catheter stylet system 104 is being inserted.

In such an embodiment, the path module 708 may determine the optimal path to the target point based on information known about the structure of the portion of the body where the catheter stylet system 104 is being inserted between the insertion point and the target point, e.g., between the opening 604 and the ventricle 603 shown in FIGS. 6A and 6B. For example, the path module 708 may reference known structural elements, materials, tissues, or other components within the user's brain to determine an optimal path through the user's brain from the bore hole to the target ventricle. The known structural elements may include structural elements that are typically present in a human brain, which the path module 708 may determine from user input, from an external source (e.g., a health website, a medical manual, or the like), from AI-generated information about a human's brain, and/or the like. The optimal path may comprise a path that is the best path through the portion of the body that causes the least disruption, damage, interference, pain, or the like, e.g., the best path that avoids vessels, tissues, or other structures.

In one embodiment, the path module 708 may further determine a trajectory of the catheter stylet system 104 relative to the target location, e.g., based on the position sensor data from the position sensor 310, and provide instructions for moving the catheter stylet system 104 along the optimal path. In other words, the path module 708 may determine if the catheter stylet system 104 is on a trajectory that deviates from the optimal path, and if so, provide feedback, instructions, directions, or the like for moving the catheter stylet system 104 to get it back on the optimal path. For instance, the path module 708 may provide audible or visual feedback (e.g., move up two millimeters, go back, move forward 4 millimeters, or the like) giving directions for moving the catheter stylet system 104 to be as close to the optimal path as possible as the catheter stylet system 104 is inserted and moved toward the target location. In one embodiment, drift away from the optimal path can be approximated by using vector summation or real-time imaging signal feedback with the 3D reconstructed graphic.

In one embodiment, the presentation module 706 displays the target location, the optimal path, and the trajectory of the catheter stylet system 104 on the display device 103. In such an embodiment, the presentation module 706 displays the target location, the optimal path, and the trajectory of the catheter stylet system 104 as an overlay over the multi-dimensional graphic of the body, with each being shown visually as a different color, pattern, brightness, or the like. Furthermore, the presentation module 706 may display instructions, directions, measurements, or the like for moving the catheter stylet system 104 to stay on the optimal path.

For example, the presentation module 706 may display an on-screen red-light/green-light target image/trajectory system to assist the surgeon to advance the catheter on a correct line. The green-light target icon would indicate to the surgeon that the catheter stylet system 104 is on the correct line/optimal path to penetrate the ventricle. The target trajectory may turn red once the trajectory has deviated from the optimal path, indicating to the surgeon that trajectory correction is needed for interception of the ventricular space.

In one embodiment, the AI module 710 is configured to use an AI engine to determine various information associated with placement of the catheter stylet system 104. As used herein, AI is broadly defined as a branch of computer science dealing in automating intelligent behavior. AI systems may be designed to use machines to emulate and simulate human intelligence and corresponding behavior. This may take many forms, including symbolic or symbol manipulation AI. AI may address analyzing abstract symbols and/or human readable symbols. AI may form abstract connections between data or other information or stimuli. AI may form logical conclusions. AI is the intelligence exhibited by machines, programs, or software. AI has been defined as the study and design of intelligent agents, in which an intelligent agent is a system that perceives its environment and takes actions that maximize its chances of success.

AI may have various attributes such as deduction, reasoning, and problem solving. AI may include knowledge representation or learning. AI systems may perform natural language processing, perception, motion detection, and information manipulation. At higher levels of abstraction, it may result in social intelligence, creativity, and general intelligence. Various approaches are employed including cybernetics and brain simulation, symbolic, sub-symbolic, and statistical, as well as integrating the approaches.

Various AI tools may be employed, either alone or in combinations. The tools may include search and optimization, logic, probabilistic methods for uncertain reasoning, classifiers and statistical learning methods, neural networks, deep feedforward neural networks, deep recurrent neural networks, deep learning, control theory and languages.

In one embodiment, the AI engine may include a generative AI engine. As used herein, generative AI is a type of AI that can create new content, such as text, images, music, audio, and videos. Generative AI systems are often used to develop synthetic data, which can be used to train machine learning models and validate mathematical models. In such an embodiment, prompts may be provided to the generative AI engine for generation of content. For example, as used herein, the AI module 710 may provide a prompt such as "generate a 3D image of an average human brain," "generate a map of different ventricles on the human brain," "generate a path from the skull to a ventricle in the human brain," or the like.

In such an embodiment, the AI module 710 may train an AI engine on subject-specific data such as brain topography or other structure-related data from a variety of patients (e.g., MRI scan data, CT scan data, images, videos, text, or the like that describe or show the structural elements for a plurality of patients). Moreover, the AI module 710 may train an AI engine on ultrasound data related to different structures to identify patterns in the ultrasound signal that are associated with different structural elements such as tissue, fluid, ventricles, vessels, bone, or the like.

Accordingly, a user may customize an AI engine for a particular application and use it to determine such things as an optimal pulse pattern for the ultrasound signal, an optimal stylet tip design for a particular portion of the body, structural components identified in a 1D signal (e.g., segmentation analysis), signal processing (e.g., to remove noise from the signal data, optimal path/trajectory analysis, and/or the like. The AI engine may further be used to assist with generation of the multi-dimensional image using the output signal data by training the AI engine to process the signal data to generate a graphical image of the signal data.

Figure 8:
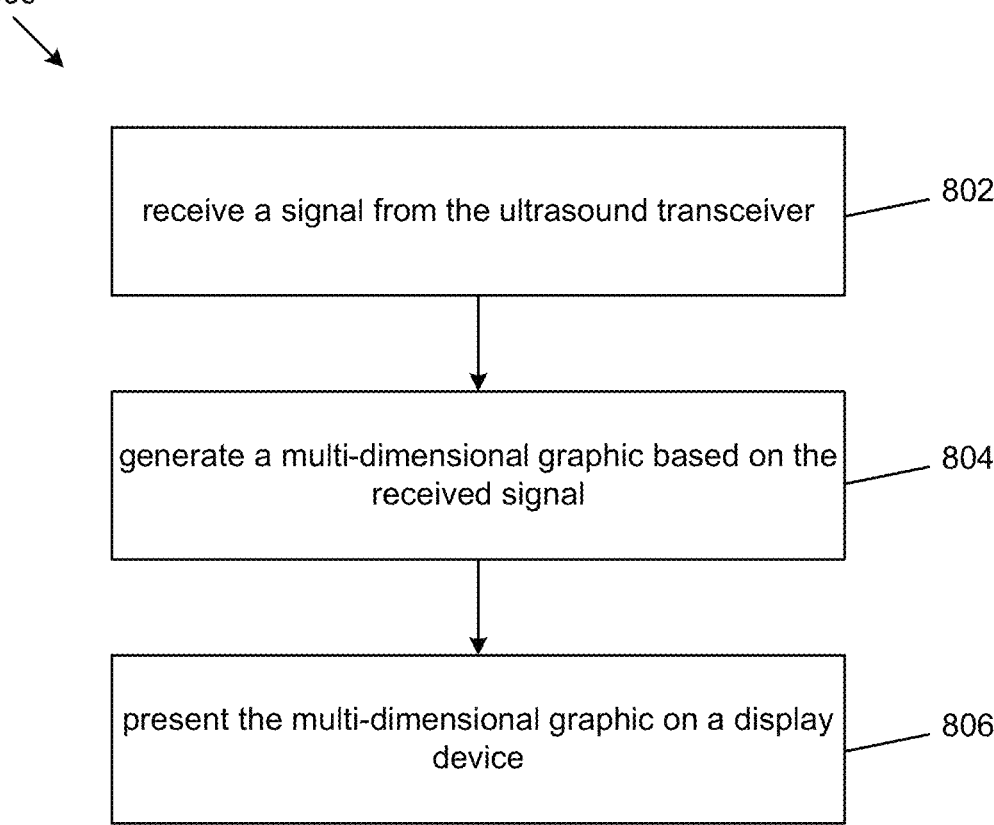
FIG. 8 depicts one embodiment of a method for an ultrasound-equipped catheter stylet system, in accordance with the subject matter disclosed herein.

FIG. 8 depicts one embodiment of a method 800 for an ultrasound-equipped catheter stylet system, in accordance with the subject matter disclosed herein. In one embodiment, the method 800 is performed by a computing device 102, a server 112, a catheter stylet system 104, an imaging apparatus 104, a signal processing module 702, a graphic generation module 704, a presentation module 706, a path module 708, an AI module 710, or a combination thereof.

In one embodiment, the method 800 begins and receives 802 a signal from the ultrasound transceiver 306, generates 804 a multi-dimensional graphic based on the received signal, and presents 806 the multi-dimensional graphic on a display device 103, and the method 800 ends.

FIG. 9 depicts one embodiment of a method 900 for an ultrasound-equipped catheter stylet system, in accordance with the subject matter disclosed herein. In one embodiment, the method 900 is performed by a computing device 102, a server 112, a catheter stylet system 104, an imaging apparatus 104, a signal processing module 702, a graphic generation module 704, a presentation module 706, a path module 708, an AI module 710, or a combination thereof.

In one embodiment, the method 900 begins and receives 902 a signal from the ultrasound transceiver 306 and generates 904 a multi-dimensional graphic based on the received signal. In one embodiment, the method 900 determines 906 an optimal path to a target location within the body.

In one embodiment, the method 900 presents 908 the multi-dimensional graphic on a display device 103. In one embodiment, the method 900 determines 910 a trajectory of the catheter stylet system 104 relative to the target location and provide instructions for moving the catheter stylet system 104 along the optimal path. In one embodiment, the method 900 updates 912 the multi-dimensional graphic in real-time in response to the change in position of the stylet, and the method 900 ends.

FIG. 10 depicts one embodiment of a method 1000 for an ultrasound-equipped catheter stylet system, in accordance with the subject matter disclosed herein. In one embodiment, the method 1000 is performed by a computing device 102, a server 112, a catheter stylet system 104, an imaging apparatus 104, a signal processing module 702, a graphic generation module 704, a presentation module 706, a path module 708, an AI module 710, or a combination thereof.

In one embodiment, the method 1000 begins and inserts 10002 a stylet 204 into a catheter 202, inserts 1004 the catheter 202 into a body, causes 1006 the ultrasound transceiver 306 in the stylet 204 to generate an ultrasound signal, moves 1008 the stylet 204 in a conical manner as the catheter 202 is inserted into the body, receives 1010 position data from a position sensor 310 in the stylet 204 and signal data from the ultrasound transceiver 306 as the stylet 204 is moved, generates 1012 a multi-dimensional graphic of a portion of the body where the catheter 202 is inserted based on the position data and the signal data, and the method 1000 ends.

An apparatus for ultrasound-equipped catheter stylet system is disclosed. A system and method also perform the functions of the apparatus. In one embodiment, an apparatus includes a catheter and a stylet configured for insertion into the catheter. The stylet, in one embodiment, includes a shaft having a first end and a second end and an ultrasound transceiver coupled to the first end of the shaft, the ultrasound transceiver configured to transmit and receive an ultrasound signal.

In one embodiment, the shaft of the stylet comprises at least one channel along a length of the shaft that creates at least one space between the catheter and the shaft when the stylet is inserted into the catheter. In one embodiment, the shaft of the stylet has a shape that is different from an inside shape of the catheter such that space is introduced between the shaft and the catheter when the stylet is inserted into the catheter.

In one embodiment, the catheter comprises an echolucent tip, the stylet inserted into the catheter such that the ultrasound transceiver is proximate to the echolucent tip. In one embodiment, the echolucent tip has a configuration that filters or focuses the ultrasound signal, the configuration comprising a shape of the echolucent tip, a size of the echolucent tip, a thickness of the echolucent tip, a presence of cavities within the echolucent tip, or a combination thereof.

In one embodiment, the ultrasound transceiver has a concave shape for focusing the ultrasound signal. In one embodiment, the ultrasound transceiver is detachable from the shaft prior to removing the stylet from the catheter.

In one embodiment, the stylet further comprises a position sensor that detects a position of the stylet relative to a fixed point. In one embodiment, the ultrasound transceiver is configured to transmit and receive A-mode ultrasound signals.

In one embodiment, a system includes a catheter and a stylet for insertion into the catheter. In one embodiment, the stylet includes a shaft having a first end and a second end, an ultrasound transceiver coupled to the first end of the shaft, the ultrasound transceiver configured to transmit and receive an ultrasound signal, and a position sensor that detects a position of the stylet relative to a fixed point. In one embodiment, the system is configured to receive a signal from the ultrasound transceiver, generate a multi-dimensional graphic based on the received signal, and present the multi-dimensional graphic on a display device.

In one embodiment, the system is configured to generate the multi-dimensional graphic based on a change in position of the stylet according to position data received from the position sensor.

In one embodiment, the system is configured to update the multi-dimensional graphic in real-time in response to the change in position of the stylet. In one embodiment, the multi-dimensional graphic comprises a multi-dimensional graphic of a portion of a body where the catheter is inserted.

In one embodiment, the system is configured to determine an optimal path to a target location within the body. In one embodiment, the system is configured to determine a trajectory of the catheter relative to the target location and provide instructions for moving the catheter along the optimal path.

In one embodiment, the system is configured to display the target location, the optimal path, and the trajectory of the catheter on the display device, overlaying a multi-dimensional graphic of the body. In one embodiment, the system is configured to visually highlight different parts of the portion of body that have different properties based on the signal received from the ultrasound transceiver.

In one embodiment, the system is configured to use an artificial intelligence engine to determine an optimal pulse pattern for the ultrasound signal. In one embodiment, the system includes an anchor device configured to stabilize the catheter at an insertion point where the catheter is inserted into a portion of the body.

In one embodiment, a method is configured to insert a stylet into a catheter, insert the catheter into a body, cause the ultrasound transceiver to generate an ultrasound signal, move the stylet in a conical manner as the catheter is inserted into the body, receive position data from the position sensor and signal data from the ultrasound transceiver as the stylet is moved, and generate a multi-dimensional graphic of a portion of the body where the catheter is inserted based on the position data and the signal data.

Reference throughout this specification to "one embodiment," "an embodiment," or similar language means that a particular feature, structure, or characteristic described in connection with the embodiment is included in at least one embodiment. Thus, appearances of the phrases "in one embodiment," "in an embodiment," and similar language throughout this specification may, but do not necessarily, all refer to the same embodiment, but mean "one or more but not all embodiments" unless expressly specified otherwise. The terms "including," "comprising," "having," and variations thereof mean "including but not limited to" unless expressly specified otherwise. An enumerated listing of items does not imply that any or all of the items are mutually exclusive and/or mutually inclusive, unless expressly specified otherwise. The terms "a," "an," and "the" also refer to "one or more" unless expressly specified otherwise.

Furthermore, the described features, advantages, and characteristics of the embodiments may be combined in any suitable manner. One skilled in the relevant art will recognize that the embodiments may be practiced without one or more of the specific features or advantages of a particular embodiment. In other instances, additional features and advantages may be recognized in certain embodiments that may not be present in all embodiments.

These features and advantages of the embodiments will become more fully apparent from the following description and appended claims or may be learned by the practice of embodiments as set forth hereinafter. As will be appreciated by one skilled in the art, aspects of the present invention may be embodied as a system, method, and/or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module," or "system." Furthermore, aspects of the present invention may take the form of a computer program product embodied in one or more computer readable medium(s) having program code embodied thereon.

Many of the functional units described in this specification have been labeled as modules, in order to more particularly emphasize their implementation independence. For example, a module may be implemented as a hardware circuit comprising custom very large scale integrated ("VLSI") circuits or gate arrays, off-the-shelf semiconductors such as logic chips, transistors, or other discrete components. A module may also be implemented in programmable hardware devices such as a field programmable gate array ("FPGA"), programmable array logic, programmable logic devices or the like.

Modules may also be implemented in software for execution by various types of processors. An identified module of program code may, for instance, comprise one or more physical or logical blocks of computer instructions which may, for instance, be organized as an object, procedure, or function. Nevertheless, the executables of an identified module need not be physically located together but may comprise disparate instructions stored in different locations which, when joined logically together, comprise the module and achieve the stated purpose for the module.

Indeed, a module of program code may be a single instruction, or many instructions, and may even be distributed over several different code segments, among different programs, and across several memory devices. Similarly, operational data may be identified and illustrated herein within modules and may be embodied in any suitable form and organized within any suitable type of data structure. The operational data may be collected as a single data set or may be distributed over different locations including over different storage devices, and may exist, at least partially, merely as electronic signals on a system or network. Where a module or portions of a module are implemented in software, the program code may be stored and/or propagated on in one or more computer readable medium(s).

The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory ("RAM"), a read-only memory ("ROM"), an erasable programmable read-only memory ("EPROM" or Flash memory), a static random access memory ("SRAM"), a portable compact disc read-only memory ("CD-ROM"), a digital versatile disk ("DVD"), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture ("ISA") instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network ("LAN") or a wide area network ("WAN"), or the connection may be made to an external computer (for example, through the Internet using an Internet Service Provider). In some embodiments, electronic circuitry including, for example, programmable logic circuitry, field-programmable gate arrays ("FPGA"), or programmable logic arrays ("PLA") may execute the computer readable program instructions by utilizing state information of the computer readable program instructions to personalize the electronic circuitry, to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/ or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

Many of the functional units described in this specification have been labeled as modules, in order to more particularly emphasize their implementation independence. For example, a module may be implemented as a hardware circuit comprising custom VLSI circuits or gate arrays, off-the-shelf semiconductors such as logic chips, transistors, or other discrete components. A module may also be implemented in programmable hardware devices such as field programmable gate arrays, programmable array logic, programmable logic devices or the like.

Modules may also be implemented in software for execution by various types of processors. An identified module of program instructions may, for instance, comprise one or more physical or logical blocks of computer instructions which may, for instance, be organized as an object, procedure, or function. Nevertheless, the executables of an identified module need not be physically located together but may comprise disparate instructions stored in different locations which, when joined logically together, comprise the module and achieve the stated purpose for the module.

The schematic flowchart diagrams and/or schematic block diagrams in the Figures illustrate the architecture, functionality, and operation of possible implementations of apparatuses, systems, methods and computer program products according to various embodiments of the present invention. In this regard, each block in the schematic flowchart diagrams and/or schematic block diagrams may represent a module, segment, or portion of code, which comprises one or more executable instructions of the program code for implementing the specified logical function(s).

It should also be noted that, in some alternative implementations, the functions noted in the block may occur out of the order noted in the Figures. For example, two blocks shown in succession may, in fact, be executed substantially concurrently, or the blocks may sometimes be executed in the reverse order, depending upon the functionality involved. Other steps and methods may be conceived that are equivalent in function, logic, or effect to one or more blocks, or portions thereof, of the illustrated Figures.

Although various arrow types and line types may be employed in the flowchart and/or block diagrams, they are understood not to limit the scope of the corresponding embodiments. Indeed, some arrows or other connectors may be used to indicate only the logical flow of the depicted embodiment. For instance, an arrow may indicate a waiting or monitoring period of unspecified duration between enumerated steps of the depicted embodiment. It will also be noted that each block of the block diagrams and/or flowchart diagrams, and combinations of blocks in the block diagrams and/or flowchart diagrams, can be implemented by special purpose hardware-based systems that perform the specified functions or acts, or combinations of special purpose hardware and program code.

As used herein, a list with a conjunction of "and/or" includes any single item in the list or a combination of items in the list. For example, a list of A, B and/or C includes only A, only B, only C, a combination of A and B, a combination of B and C, a combination of A and C or a combination of A, B and C. As used herein, a list using the terminology "one or more of" includes any single item in the list or a combination of items in the list. For example, one or more of A, B and C includes only A, only B, only C, a combination of A and B, a combination of B and C, a combination of A and C or a combination of A, B and C. As used herein, a list using the terminology "one of" includes one and only one of any single item in the list. For example, "one of A, B and C" includes only A, only B or only C and excludes combinations of A, B and C. As used herein, "a member selected from the group consisting of A, B, and C," includes one and only one of A, B, or C, and excludes combinations of A, B, and C. As used herein, "a member selected from the group consisting of A, B, and C and combinations thereof" includes only A, only B, only C, a combination of A and B, a combination of B and C, a combination of A and C or a combination of A, B and C.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:
1. An apparatus, comprising:
a catheter; and
a stylet configured for insertion into the catheter, the stylet comprising:
    a shaft having a first end and a second end, wherein the shaft comprises at least one channel along a length of the shaft that creates at least one space between the catheter and the shaft when the stylet is inserted into the catheter; and an ultrasound transceiver coupled to the first end of the shaft, the ultrasound transceiver configured to transmit and receive an ultrasound signal.

2. The apparatus of claim 1, wherein the shaft of the stylet has a shape that is different from an inside shape of the catheter such that space is introduced between the shaft and the catheter when the stylet is inserted into the catheter.

3. The apparatus of claim 1, wherein the catheter comprises an echolucent tip, the stylet inserted into the catheter such that the ultrasound transceiver is proximate to the echolucent tip.

4. The apparatus of claim 3, wherein the echolucent tip has a configuration that filters or focuses the ultrasound signal, the configuration comprising a shape of the echolucent tip, a size of the echolucent tip, a thickness of the echolucent tip, a presence of cavities within the echolucent tip, or a combination thereof.

5. The apparatus of claim 1, wherein the ultrasound transceiver has a concave shape for focusing the ultrasound signal.

6. The apparatus of claim 1, wherein the ultrasound transceiver is detachable from the shaft prior to removing the stylet from the catheter.

7. The apparatus of claim 1, wherein the stylet further comprises a position sensor that detects a position of the stylet relative to a fixed point.

8. The apparatus of claim 1, wherein the ultrasound transceiver is configured to transmit and receive A-mode ultrasound signals.

9. A system, comprising:
  a catheter;
  a stylet configured for insertion into the catheter, the stylet comprising:
    a shaft having a first end and a second end, wherein the shaft comprises at least one channel along a length of the shaft that creates at least one space between the catheter and the shaft when the stylet is inserted into the catheter;
    an ultrasound transceiver coupled to the first end of the shaft, the ultrasound transceiver configured to transmit and receive an ultrasound signal; and
    a position sensor that detects a position of the stylet relative to a fixed point;
  a memory; and
  a processor coupled with the memory and the stylet, the processor configured to:
    receive a signal from the ultrasound transceiver;
    generate a multi-dimensional graphic based on the signal; and
    present the multi-dimensional graphic on a display device.

10. The system of claim 9, wherein the processor is configured to generate the multi-dimensional graphic based on a change in position of the stylet according to position data received from the position sensor.

11. The system of claim 10, wherein the processor is configured to update the multi-dimensional graphic in real-time in response to the change in position of the stylet.

12. The system of claim 9, wherein the multi-dimensional graphic comprises a multi-dimensional graphic of a portion of a body where the catheter is inserted.

13. The system of claim 12, wherein the processor is configured to determine an optimal path to a target location within the body.

14. The system of claim 13, wherein the processor is configured to determine a trajectory of the catheter relative to the target location and provide instructions for moving the catheter along the optimal path.

15. The system of claim 14, wherein the processor is configured to display the target location, the optimal path, and the trajectory of the catheter on the display device, overlaying a multi-dimensional graphic of the body.

16. The system of claim 12, wherein the processor is configured to visually highlight different parts of the portion of the body that have different properties based on the signal received from the ultrasound transceiver.

17. The system of claim 9, wherein the processor is configured to use an artificial intelligence engine to determine an optimal pulse pattern for the ultrasound signal.

18. The system of claim 9, further comprising an anchor device configured to stabilize the catheter at an insertion point where the catheter is inserted into a portion of a body.

19. The system of claim 9, wherein the shaft of the stylet has a shape that is different from an inside shape of the catheter such that space is introduced between the shaft and the catheter when the stylet is inserted into the catheter.

20. A method, comprising:
  inserting a stylet into a catheter, the stylet comprising:
    a shaft having a first end and a second end, wherein the shaft comprises at least one channel along a length of the shaft that creates at least one space between the catheter and the shaft when the stylet is inserted into the catheter;
    an ultrasound transceiver coupled to the first end of the shaft, the ultrasound transceiver configured to transmit and receive an ultrasound signal; and
    a position sensor that detects a position of the stylet relative to a fixed point;
  inserting the catheter into a body;
  causing the ultrasound transceiver to generate the ultrasound signal;
  moving the stylet in a conical manner as the catheter is inserted into the body;
  receiving position data from the position sensor and signal data from the ultrasound transceiver as the stylet is moved; and
  generating a multi-dimensional graphic of a portion of the body where the catheter is inserted based on the position data and the signal data.

* * * * *